United States Patent [19]

Webb et al.

[11] Patent Number: 4,746,539
[45] Date of Patent: May 24, 1988

[54] PURIFICATION OF CANCER-ASSOCIATED PROTEIN AND PREPARATION OF ANTIBODY THERETO

[75] Inventors: Thomas E. Webb; Dorothy E. Schumm; Margaret Hanausek-Walaszek, all of Columbus, Ohio

[73] Assignee: The Ohio State University Research Foundation, Columbus, Ohio

[21] Appl. No.: 554,439

[22] Filed: Nov. 23, 1983

[51] Int. Cl.$^4$ .................. C12Q 1/00; C12P 21/00; C12P 21/02; A61K 39/00
[52] U.S. Cl. ......................................... 424/85; 435/7; 435/68; 435/70; 435/29; 514/2; 514/6; 424/88; 530/352; 530/828; 530/830; 436/548
[58] Field of Search ...................... 424/85, 88, 177; 260/112 B, 112 R; 436/545, 506, 548; 435/68, 70, 7, 29; 514/2, 6; 530/350, 352, 828, 830

[56] References Cited

U.S. PATENT DOCUMENTS

| 4,126,671 | 11/1978 | House et al. |
| 4,160,019 | 7/1979 | Bjorklund. |
| 4,264,589 | 4/1981 | Felts et al. ........................ 424/99 |
| 4,270,924 | 6/1981 | Crooke et al. |
| 4,288,540 | 9/1981 | Turcotte. |
| 4,317,877 | 3/1982 | Balis et al. |

FOREIGN PATENT DOCUMENTS 2067286A 7/1981 United Kingdom .................. 530/35

OTHER PUBLICATIONS

Durban et al, Cancer Research, vol. 41, pp. 535–545, Feb. 1981, "Purification and Characterization of Nuclear DNA-Binary Phosphoprotein in Fetal and Tumor Tissues".
Schumm et al, J. Nat. Cancer Inst. vol. 54, pp. 123–128, 1975, "Modification of Nuclear Restriction in Vitro by Plasma from Tumor-Bearing Animals".
Tamura et al, Cell, vol. 34, pp. 587–596, Sep. 1983, "Antibodies Against Synthetic Peptides as a Tool for Functional Analysis of the Transforming Protein, p. 60".
Leppard et al, EMBO Journal, vol. 2(9), Sep. 1983, pp. 1457–1464, "Monoclonal Antibodies Displaying a Novel Species Specificity for the Primatic Transformation Protein p. 53".
Walaszek et al., Biol. Abstracts, No. 7658, Oct. 1983, "An Oncofetal 60-Kilodlalton Protein on the Plasma of Tumor Bearing and Carcinogen Treated Mice".
Davis et al, "Differences in Nucleolar Antigens of Rat Liver and Novikoff Hepatoma Ascites Cells" in Cancer Research 38, 1900–1915, Jul. 1978.
Farhad Marashi et al., "Purification and Partial Characterization of Nucleolar Antigen-1 of the Novikoff Hepatoma" in Cancer Research 39, 59–66, Jan. 1979.

(List continued on next page.)

Primary Examiner—Thomas G. Wiseman
Assistant Examiner—Robin Lyn Teskin
Attorney, Agent, or Firm—Wegner & Bretschneider

[57] ABSTRACT

It has previously been shown that the serum from patients suffering from a wide range of cancers contains a cancer marker protein having the ability to release RNA from cell nuclei. This cancer marker protein is purified by taking the protein fraction precipitating between 30% and 50% saturated aqueous ammonium sulfate solution, dialyzing a solution of the protein fraction against TMK buffer, chromatographing the dialyzed protein on a molecular sieve and isolating the fraction having a molecular weight of about 60,000; and removing albumin. Injection of the purified protein into rabbits, preparation of serum from blood of the rabbits and absorption of the sera with normal plasma fraction produces at antibody specific to the cancer marker protein and therefore useful in a radioimmunoassay or ELISA test for a wide variety of cancers. Monoclonal antibody preparations to the protein may be prepared by injecting the purified protein into mice, harvesting the spleen and lymph node cells, fusing these cells with mouse myeloma cells and using the resultant hybridoma cells to produce the monoclonal antibody.

22 Claims, 1 Drawing Sheet

OTHER PUBLICATIONS

Frances M. Davis et al, "Nucleolar Antigen Found in Several Human Tumors But Not in the Nontumor Tissues Studied" in Proc. Natl. Acad. Sci., USA, vol. 766, No. 2, pp. 892–896, Feb. 1979.

Harris Busch et al., "A Nucleolar Antigen Found in a Broad Range of Human Malignant Tumor Specimens" in Cancer Research 39, 3024–3030, Aug. 1979.

Jo Hilgers et al., "Detection of Avian and Mammalian Oncogenic RNA Viruses (Oncornaviruses) by Immunofluorescence" in Cancer Research 32, 98–106, Jan. 1972.

Rose K. Busch et al. "Rabbit Antibodies to Nucleoli of Novikoff Hepatoma and Normal Liver of the Rat" in Cancer Research 34, 2362–2367, Sep. 1974.

Karel Smetana et al., "Nucleolar Immunofluorescence in Human Hematological Malignancies" in Life Sciences, vol. 25, pp. 227–234.

Bio-Rad Laboratories, price list G, Feb. 1981, front sheet and pp. 40, 43 and index page.

Nature New Biology, 245, 201–203 (1973).

Biochem. J., 139, 191–196 (1974).

Schumm et al, Biochem. Biophys. Res. Comm. 48:1259 (1972).

Cancer Res., 33:1821 (1973).

Biochem. Biophys. Res. Comm., 58:354 (1974).

Biochem. J., 154:379 (1976).

Nature, 256:508 (1975).

Der et al., "A Tumor-Specific Membrane Phosphoprotein Marker in Human Cell Hybrids", Cell, vol. 26, 429–438, Nov. 1981.

Schumm et al., "Absence of the Cancer-Associated Factor with a Molecular Weight of 60,000 from the Plasma of Patients with a Spectrum of Nonneoplastic Conditions," Cancer Research 44, 401–406, Jan. 1984.

Hanausek-Walaszek, et al., "Characterizatin of a 60,00-Dalton Circulated Oncofetal Protein from the Plasma of Tumor-Bearing Rats", Cancer Investigation, 2(6), 433–441 (1984).

French et al., "Nucleocytoplasmic Release of Repetitive DNA Transcripts in Carcinogenesis Correlates with a 60 Kilodalton Cytoplasmic Protein", Cancer Letters, 23, 45–52 (1984).

Walaszek, et al., "Inhibition of 7,12-Dimethylbenzanthracene-Induced Rat Mammary Tumorigenesis by 2,5-Di-)-Acetyl-D-Glucaro-1,4:6,3-Dilactin, an in vivo-Glucoronidase Inhibitor", Carcinogenesis, 5(6), 767–772, (1984).

Hanausek-Walaszek et al., "Immunological Indentity of a 60 KD Oncofetal Protein Induced in Rats by Chemical Carcinogens and Released by Transformed Cells", Biochem. Biophys. Res. Comm. 127(3), 777–785, Mar. 29, 1985.

Walaszek et al., "An Oncofetal 60-kilodalton Protein in the Plasma of Tumor-Bearing and Carcinogen-Treated Rats", Cancer Letters, 20, 277–282 (1983).

Schumm et al., "Putative Transformation-Dependent Proteins in the Blood Plasma of Tumor-Bearing Rats and Cancer Patients", Cancer Research, 42, 4964–4969, Dec. 1982.

Schumm et al., "Apparent Transformed Cell-Dependent Proteins in Blood Plasma", Abstract No. 313 of American Association of Cancer Research (1981).

Schumm et al., "Changes in Nuclear RNA Transport Incident to Carcinogenesis", Eur. J. Cancer, 13, 139–147 (1977).

PURIFICATION OF CANCER-ASSOCIATED PROTEIN AND PREPARATION OF ANTIBODY THERETO

The United States has certain rights in this invention pursuant to grants CA 30627 and P-30-CA-16058-09 by the National Institutes of Health.

BACKGROUND OF THE INVENTION

This invention relates to the purification of a cancer-associated protein and to the preparation of an antibody thereto.

In spite of improved treatments for certain forms of cancer, it is still the second leading cause of death in the United States. Since the chance for complete remission of cancer is, in most cases, greatly enhanced by early diagnosis, it is very desirable that physicians be able to detect cancers before a substantial tumor develops. Also, in cases where the primary tumor has been substantially removed by surgery or destroyed by other means, it is important that the physician be capable of detecting any trace of cancer in the patient (either in the form of residues of the primary tumor or of secondary tumors caused by metastasis), in order that the physician can prescribe appropriate subsequent treatment, such as chemotherapy.

The quantities of cancer cells that must be detected for early diagnosis or following removal or destruction of the primary tumor are so small that the physician cannot rely upon physical examination of the cancer site; moreover, in many cases the cancer site is of course not susceptible of direct visual observation and it is almost always impractical to detect secondary tumors by visual observation, since it is not possible to predict exactly where they are likely to occur. Accordingly, sensitive tests have to rely upon detection of cancer-associated materials, usually proteins, present in body fluids of patients who have, or are about to develop, small numbers of cancer cells in their bodies. Diagnostic materials for detection of at least two cancer-associated proteins are already available commercially. Tests for alpha-fetoprotein are used to detect primary liver cancer and teratocarcinoma in humans; see, for example:

Abelev, Production of Embryonal Serum Alpha-Globulin by Hepatomas: Review of Experimental and Clinical Data, Cancer Res. 28: 1344-1350 (1968);

Abelev et al, Embryonal Serum Alpha-Globulin in Cancer Patients: Diagnostic Value, Int. J. Cancer, 2: 551-558 (1967); and Esterhay et al, Serum Alpha-Fetoprotein Concentration and Tumor Growth in a Patient with Ovarian Teratocarcinoma, Cancer (Philadelphia), 31: 835-839 (1973).

Similarly, carcinoembryonic antigen is used for diagnosis of cancers of the digestive system; see, for example:

Gold and Freedman, Demonstration of Tumor-Specific Antigens in Human Colonic Carcinomata by Immunological Tolerance and Absorption Techniques, J. Exp. Med., 121: 439-462 (1965); and Terry et al, Carcinoembryonic Antigen: Characterization and Clinical Applications, Transplant Rev., 20: 100-129 (1974).

Unfortunately, both the aforementioned tests are only applicable to a narrow range of cancer types, and therefore these tests suffer not only from the disadvantage that other types of cancer may be missed but also from the disadvantage that the narrow applicability of the tests means that it may be necessary to run multiple tests on a single patient for diagnostic purposes, a procedure which not only increases the expense of the diagnostic testing but also increases the risk that one or other of the tests may give a false positive result. Accordingly, there is a need for a single chemical test able to detect the presence of very small amounts of cells of a wide variety of different cancers.

It is already known that serum from the blood of animals suffering from a wide variety of cancers contains a protein (hereinafter referred to as "cancer marker protein") having a molecular weight of approximately 60,000 and having the capacity to increase the release of ribonucleic acid (RNA) from cell nuclei; see:

Schumm et al, Apparent Transformed Cell-dependent Proteins in Blood Plasma, Proc. Am. Assoc. Cancer Res., 22: 79 (1981);

Schumm and Webb, Differential Effect of Plasma Fractions from Normal and Tumor-Bearing Rats on Nuclear RNA Restriction, Nature (London), 256: 508-509 (1975);

Schumm and Webb, Modification of Nuclear Restriction In Vitro by Plasma from Tumor-Bearing Animals, J. Natl. Cancer Inst., 54: 123-128 (1975); and Schumm and Webb, Apparent Transformed Cell-Dependent Proteins in Blood Plasma, Proc. Am. Assoc. Cancer Res., 22: 79 (1981).

Thus, testing for this cancer marker protein is a potential, sensitive method for the detection of a wide variety of cancers in humans and other mammals. Unfortunately, the only method of detecting this cancer marker protein described in the aforementioned papers involves assaying the ability of serum protein from the patient being tested to release RNA from rat liver nuclei; see:

Schumm et al, Changes in Nuclear RNA Transport Incident to Carcinogenesis, Eur. J. Cancer, 13: 139-147 (1977);

Schumm et al, Cytosol-Modulated Transport of Messenger RNA from Isolated Nuclei Cancer Res., 33: 1821-1828 (1973).

Although, as shown in the aforementioned papers, this test is capable of detecting cancer in patients, the assaying method used is not suitable for routine use by medical technicians. Accordingly, there is a need for a simpler, less costly test for detection of this cancer marker protein.

One method often used for detection of proteins and other antigens is radioimmunoassay. In this technique, a sample of the material to be assayed is mixed with a known quantity of a radioactive-labeled form of the antigen to be measured. The resultant mixture is then treated with an antibody to the antigen being assayed, thereby forming an antigen-antibody complex. The degree of radioactivity of this complex depends upon the amount of the appropriate antigen in the sample being assayed and thus, by measuring the radioactivity of the complex, the quantity of the antigen in the sample may be determined. Radioimmunossay techniques are suitable for routine use by medical technicians and indeed are already used for assay of a variety of antigens in various body fluids. Thus, radioimmunoassay is potentially an attractive technique for testing for the cancer marker protein. However, a radioimmunoassay technique requires the prior preparation of an antibody which is specific to the antigen being assayed and the aforementioned papers do not describe any method for the preparation of such an antibody. Moreover, to prepare an antibody specific to the cancer marker protein, it is necessary to prepare the cancer marker protein in a relatively pure form, since the antibodies have to be prepared by injecting the cancer marker protein into an animal and recovering serum therefrom, and any impurities in the cancer marker protein may give rise to corresponding antibodies to those impurities, thereby interfering with the accurate assay of the cancer marker protein in the radioimmunoassay test.

Another method for the detection of proteins and other antigens is known as an ELISA assay. In this assay, the walls of wells in a culture plate are coated with an antibody to the antigen to be assayed and the wells are then washed. A specimen of the material to be tested is placed in the coated wells, incubated for a period sufficient to allow any antigen present to react with the antibody on the walls, and after incubation the wells are again washed out. Next, there is added to the wells a conjugate of the antibody and horseradish peroxidase, the plates are incubated and washed out, and a mixture of hydrogen peroxide in a buffer and 2,2'-AzinoDi(3-Ethylbenzthiazoline sulfonic Acid) (ABTS) and the plates are allowed to develop for ten minutes at room temperature. The reaction was then stopped by the addition of 2 mM sodium azide solution. If the antigen being assayed (i.e. that specific to the antibody) is not present in the test material, no color will be formed in the wells of the plates because the peroxidase enzyme will have been washed away. If, however, the antigen being assayed is present in the test material immunological reactions will cause the enzyme to adhere to the walls of the wells and this enzyme will cause formation of a color with the hydrogen peroxide/ABTS mixture. Thus, the formation of color at the end of the test is indicative of the presence of the antigen. Like radioimmunoassay, this assay technique requires the preparation of an antibody specific to the antigen being assayed and the preparation of this antibody requires purification of the antigen.

Accordingly, there is a need for a method of preparing the cancer marker protein in a relatively pure form and a method for producing an appropriate antibody to this cancer marker protein. This invention seeks to meet these requirements.

SUMMARY OF THE INVENTION

This invention provides a protein preparation containing a relatively pure form of the aforementioned cancer marker protein. More specifically, the invention provides a protein preparation comprising a cancer-associated phosphoprotein having the following characteristics:
  (a) not being precipitated by 30% saturated aqueous ammonium sulfate solution at 25° C.;
  (b) having a molecular weight of approximately 60,000;
  (c) being precipitated from aqueous solution by 3.3% streptomycin sulfate;
  (d) having substantially no autophosphorylation activity but being phosphorylated with adenosine triphosphate in the presence of an exogenous protein kinase;
  (e) having substantially no protein kinase activity;
  (f) having the capacity to liberate ribonucleic acid from cell nuclei; and
  (g) being substantially free of albumin.

In addition, the instant protein preparation has an RNA-releasing activity of at least about 10 units per milligram of total protein in the preparation when assayed by the test described in the following paragraph.

The term "RNA-releasing activity" as used herein refers to activity determined by the following procedure. Male Sprague-Dawley rats weighing approximately 250 grams are fasted for 18 hours. For the preparation of cytosol, the rat livers are dissected out, homogenized in a volume of 0.25M sucrose-TMK buffer which is twice the wet weight (milliliters/gram) of the livers.

The TMK buffer used has the following composition:
  50 mM tris (hydroxy methyl amino) methane hydrochloride
  25 mM potassium chloride
  2.5 mM magnesium chloride This buffer has a pH of 7.5.

The homogenate is centrifuged at 100,000 g for 90 minutes and the supernatant removed and dialyzed overnight against TMK buffer.

For the preparation of neclei, rats are injected with 50 micro curies of [6-$^{14}$C] orotic acid (specific activity 323 micro curies/milligram; this material is available from New England Nuclear Corporation, Boston, Mass.) as described in the aforementioned paper in Cancer Res., 33: 1821–1828 (1973). After a 30 minute prelabelling, the rat livers are dissected out, homogenized in a volume of 2.3M sucrose 3.3 mM calcium acetate aqueous solution which is 15 times the weight of the liver. This homogenate is centrifuged at 34,000 g for 60 minutes at 4° C. The nuclear pellet is washed with a solution containing 1M sucrose/1 mM calcium acetate and resuspended in the same solution.

The cytosol remaining after dialysis is then used to prepare a cell-free system containing $5 \times 10^6$ prelabeled nuclei per milliliter of medium containing 5 milligram of dialyzed cytosol protein per milliliter and having the following additional components:
  50 mM Tris-HCl (pH 7.5)
  25 mM potassium chloride
  2.5 mM magnesium chloride
  0.5 mM calcium chloride
  0.3 mM manganese chloride
  5.0 mM sodium chloride
  2.5 mM phosphoenol pyruvate
  35 units/milliliter of pyruvate kinase
  2.5 mM sodium dihydrogen phosphate
  5.0 mM spermidine
  2.0 mM dithiothreitol
  2.0 mM adenosine triphosphate
  300 microgram/milliliter of low molecular weight yeast RNA.

An aliquot of up to 100 microliters of plasma or 200 microliters of a column fraction containing the cancer marker protein is added to 1 milliliter of the cell-free medium and incubated at 30° C. for 30 minutes. The nuclei are removed by centrifugation, the resulting supernatant liquor separated and the RNA and protein precipitated therefrom with a 5% aqueous solution of trichloroacetic acid. The resultant precipitate is washed in ethanol, dissolved in solubilizer and counted in liquid scintillant. The preferred solubilizer is "Unisol" and the preferred scintillant "Unisol Complement", both available from Isolab, Inc., Akron, Ohio. A control is treated in the same manner, except of course, that none of the specimen being tested is added thereto. One unit of activity represents an increase in the count of 1% of the total nuclear counts and, for obvious reasons, results are normally expressed as units of activity per milligram of protein added to the test material.

This invention also provides a process for preparing a purified cancer-associated phosphoprotein, this process comprising:

(a) separating from the plasma of a mammal suffering from cancer the fraction of plasma protein which is not precipitated by 30% saturated aqueous ammonium sulfate solution;

(b) dispersing this fraction of plasma protein in a buffer and dialyzing the resultant protein solution against the buffer;

(c) separating the fraction of the dialyzed protein having a molecular weight of about 60,000; and (d) removing substantially all albumin from the 60,000 molecular weight fraction.

This invention also provides a process for producing a serum containing antibodies to the aforementioned cancer-marker protein, this process comprising introducing into the bloodstream of a mammal the instant protein preparation, allowing this protein preparation to remain in the bloodstream of the mammal for at least seven days, removing blood from the mammal and preparing serum from this blood.

This invention provides a process for producing a monoclonal antibody preparation containing antibodies to the instant cancer-associated phosphoprotein, this process comprising introducing into the bloodstream of a mouse the instant protein preparation, allowing the protein preparation to remain in the mouse for at least about one day, removing spleen and/or lymph node cells from the mouse, fusing these removed cells with mouse myeloma cells and culturing the resultant hybridoma cells, selecting one or more hybridoma cells capable of producing the desired antibody and harvesting this antibody from the selected cell or cells.

Finally, the invention provides an antibody preparation substantially free of antibodies to normal plasma fraction, this antibody preparation being precipitated by 35% saturated aqueous ammonium sulfate solution and capable of forming a conjugate with the instant cancer-associated phosphoprotein. The antibody preparation is capable of forming a visible precipitate with the cancer marker protein when they are diffused toward one another in agar gel but is not capable of forming a conjugate with the 25K protein fraction from human plasma nor the 35K protein fraction from rat plasma.

DETAILED DESCRIPTION OF THE INVENTION

As already mentioned, this invention provides a protein preparation comprising a purified form of the aforementioned cancer marker protein and having an RNA-releasing activity of at least 10 units per milligram of total protein in the preparation. The RNA-releasing activity of the instant protein preparation is desirably about 10 units per milligram of total protein in the preparation. Typically, in the purification of the cancer marker protein from humans, the dialyzed protein from the second step of the purification process will have an activity of about 0.84 units per milligram of protein, the 60,000 molecular weight fraction from the third step of the purification process will have an activity of about 2.66 units per milligram of total protein and the final material will have an activity of about 20 units per milligram of protein. In the purification of the cancer marker protein from rats, the dialyzed protein from the second step will have an activity of about 1.4 units per milligram, the 60,000 molecular weight fraction from the third step will have an activity of about 8.1 units per milligram and the final material will have an activity of about 71 units per milligram. It should be noted that one cannot correlate the increase in specific activity of the protein during the various stages of the purification process directly with the degree of purification affected, since it appears that the cancer marker protein does lose some of its RNA-releasing activity during the purification process, and especially in the final step thereof. It is necessary that the protein preparation be substantially free of albumin since albumin is strongly immunogenic and thus any albumin in the instant protein preparation would produce antibody serum heavily contaminated with albumin antibodies.

Although the characteristics are already specified are believed to define the instant cancer marker protein uniquely, it should be noted that various other properties of the cancer marker protein have been observed and further characterize this protein. The cancer marker protein is fairly stable, retaining full biochemical activity and showing little or no change in size during storage in plasma at −20° C. for at least three years. However, the protein is heat-labile, being completely destroyed by heating to 65° C. for 10 minutes. The protein has little or no single strand ribonuclease activity and electrophoresis on sodium dodecyl sulfatepolyacrylamide gel suggests that it consists of a single polypeptide chain since a single band appears in the 60,000 molecular weight region.

As already mentioned, the first stage in the instant method for preparing the purified cancer marker protein is separating from the serum of a mammal suffering from cancer the fraction of serum protein which is not precipitated by 30% saturated aqueous ammonium sulfate solution. Since the purpose of the ammonium sulfate precipitation step is to remove low molecular weight material, one can use the whole fraction precipitating between 30% and 100% saturation. However, in general it is preferred to use the fraction precipitating between 30% and 60% saturation, since this fraction contains substantially all the cancer marker protein.

The instant cancer marker protein preparations can be isolated from both humans and other mammals, and the protein preparations from different species appear to be generally similar in molecular weight and other chemical properties. However, the cancer marker proteins from different species are not immunologically equivalent e.g. an antibody to the rat cancer marker protein does not cross-react with a human cancer marker protein. Thus, when the purified cancer marker protein preparation is to be used for production of antibodies for diagnostic purposes, it is necessary to begin the preparation process with plasma from the species in which the diagnosis is to be used.

The second, dialysis step of the instant purification process is desirably conducted at a pH in the range of about 7 to about 8. In a particularly preferred embodiment of the invention, the dialysis is conducted by dispersing the plasma protein fraction in a tris(hydroxymethylamino)methane/potassium chloride/magnesium chloride buffer having a pH of about 7.5 and dialyzing the resultant protein solution against the same buffer. Overnight dialysis normally provides sufficient purification in this step of the instant process.

In the third step of the instant purification process, the fraction of the protein having a molecular weight of about 60,000 is separated. Although, as already noted, the molecular weight of the cancer marker protein is about 60,000, the fractions eluting in the molecular weight range of 55,000 to 70,000 should usually be collected to ensure reasonably complete recovery of the protein. Separation of the 60,000 molecular weight fraction of protein can be achieved using centrifugation, but it is preferred that this separation be effected by chromatography of the dialyzed protein from the second step of the instant process on a molecular sieve solid phase. Those skilled in the art will be aware of a variety of molecular sieve materials which can be used for this purpose; the preferred molecular sieve material is the cross-linked resin available commercially under the trade name Sepharose CL-6B. The liquid phase in the chromatography process is preferably the same TMK buffer used in the aforementioned preferred embodiment of the dialysis step. However, following the chromatography step the purified cancer marker protein is still contaminated by a considerable amount of serum albumin (molecular weight about 68,000). Accordingly, to remove this impurity it is preferred that the instant purification process includes the step of treating the 60,000 molecular weight protein fraction obtained from the third step to remove albumin therefrom. The preferred method for removal of albumin without causing any deleterious effects on the cancer marker protein itself is chromatography on a solid medium capable of absorbing alumin, and a preferred medium for this purpose is that available commercially under the trade name CM Affi-Gel Blue (obtainable from Bio-Rad Lab., Richmond, Calif.). CM Affi-Gel Blue is, as stated in the February 1981 edition of Bio-Rad Price List G, page 40, a beaded, cross-linked agarose gel containing both Cibacrom Blue F3GA groups of the formula Structure of Affi-Gel Blue $R_1$ = H or $SO_2ONa$
$R_2$ = $SO_2ONa$ or H wherein $R_1$ and $R_2$ are each hydrogen or an $SO_2ONa$ group, and pendant carboxymethyl (—$OCH_2COOH$) groups.

It should be noted that, once one batch of the purified cancer marker protein has been isolated and a serum containing antibodies thereto produced, the purification of later batches of cancer marker protein can be enhanced by treating the purified cancer marker protein isolated from the molecular sieve chromatography step (before or after removal of albumin therefrom) with the antibody-containing serum. As those skilled in the art are aware, this treatment will cause precipitation of a cancer marker protein/antibody complex which can then be separated, for example by centrifugation, and broken down by methods familiar to those skilled in the art to yield the purified cancer marker protein and the antibody; for example the protein/antibody complex may be broken down on a column of protein A agarose (sold by BRL, Gaithersburg, MD; directions for use of this material are supplied by the manufacturer).

As already mentioned, to produce a serum containing antibodies to the cancer marker protein, the purified protein is introduced into the bloodstream of a mammal and allowed to remain in the mammal for at least seven days, blood is removed from the mammal and serum prepared from this blood. To produce high levels of antibodies to the cancer marker protein, it is preferred that the purified protein be introduced into the bloodstream of the mammal together with an immunostimulating adjuvant, complete or incomplete Freund's adjuvant being efficacious for this purpose. The purified protein is desirably introduced into the mammal by intradermal injection, and a preferred administration routine comprises a primary immunization with the purified cancer marker protein and immunostimulating adjuvant, followed by a second immunization with the protein preparation and an immunostimulating adjuvant at least seven days after the primary immunization, the blood being removed from the mammal at least three days after the second immunization. A convenient mammal for use in the process is a rabbit. In order to produce an antibody-containing serum which is specific for the cancer marker protein, the serum prepared from the blood of the immunized mammal is absorbed with normal plasma fraction, thereby eliminating all antibodies produced to normal components of plasma that have carried through the purification process, and producing a purified antibody preparation that is specific to the cancer marker protein. (Even after the instant purification process, the cancer marker protein still contains traces of immunogenic impurities, so that the antibody produced by passage through the mammal is polyclonal. The absorption with normal plasma fraction removes the antibodies to normal plasma components, thereby ensuring that the antibodies are specific for the cancer marker protein and will not react with normal plasma components to give false positive results when the antibody is used for diagnostic tests as described below.) The antibody produced after absorption with normal plasma fraction gives a single precipitin line when reacted with the cancer marker protein and thus appears to be monospecific for the cancer marker protein.

As an alternative to the aforementioned procedure for producing the cancer marker protein antibody, the instant cancer marker protein preparation may be used for production of a monoclonal antibody. For this purpose, the cancer marker protein preparation is injected into mice, a booster injection is given a short time later and at least one, and preferably at least three days later, the spleen and/or lymph node cells are harvested from the mice. These cells are fused with mouse myeloma cells in the conventional manner known to those skilled in the art. The resultant hybridoma cells are grown in HAT(hypoxanthine, aminopterin, thymidine) medium and single cell clones positive for the production of the desired antigen are selected and cultured. (Selection of the desired clones can be effected using the ELISA assay system described below.)

The antibody thus prepared may be used to test for the presence of cancer marker protein in serum from suspected cancer patients by a variety of conventional tests. Thus, the antibody may be used in a radioimmunoassay, the technique for which has already been described above. The radio-labeled cancer marker protein needed for this test may be prepared from the instant cancer marker protein preparation using a procedure described by Ganguli and Hunter in Radioimmune Assay Methods (European Workshop, 1970). This radio-labeling technique involves mixing sodium iodide containing $^{125}I$ phosphate buffer having a pH of 7.5, the cancer marker protein and chloramine T, incubating for 30 seconds and stopping the labeling reaction with metabisulfate and potassium iodide. The radio-labeled cancer marker protein can be separated from the reaction mixture by chromatography on Sephadex G-50.

Alternatively, the instant antibody may be used in an ELISA assay. The preferred technique for carrying out such an assay with the instant antibody is as follows. The instant antibody is purified using a 35% solution of ammonium sulfate by the standard precipitation/-resolubilization technique and part of the antibody is then conjugated to horseradish peroxidase by the conventional techniques used in ELISA assays. Conveniently, conjugation of the horseradish peroxidase to the antibody is effected using 1-fluoro-2,4-dinitrobenzene (FDNB). A 1% solution of FDNB in absolute ethanol is mixed with the horseradish peroxidase in a bicarbonate buffer, and the resultant mixture incubated. After this incubation, ethylene glycol is added to the solution, which is then dialyzed against the bicarbonate buffer to yield horseradish peroxidase aldehyde. The antibody-containing serum fraction obtained by salt precipitation and dialysis of antibody-containing serum is added to the horseradish peroxidase aldehyde solution. After reaction is complete, sodium borohydride is added to the solution, which is then dialyzed overnight against a phosphate-buffered saline solution. The dialyzed solution is chromatographed on Sephadex G-200 gel; the first protein peak eluting from the column is the desired horseradish peroxidase/antibody conjugate. A base coat of the unconjugated portion of the antibody is deposited in the wells of a Dyntech Immulon II microelisa plate by allowing 100 microliters containing several micrograms of the antibody to remain in each well overnight at 4° C. Thereafter, the wells are washed three times and then 100 microliters of test serum from the patient added to each well (for obvious reasons, the tests are normally run in duplicate). If the cancer marker protein is present in the test serum, it will conjugate to the antibody already stuck to the walls of the cell and will thus deposit the cancer marker protein on the walls of the well. To permit the conjugation between the antibody on the walls of the cell and any cancer marker protein in the test serum, the plates are incubated at 37° C. for one hour and, at the end of this time, washed three times. Next, 100 microliters containing several micrograms of the antibody conjugated to the peroxidase are added to each well and the plates again incubate at 37° C. for one hour. As already described, if the test serum contains cancer marker protein, this cancer marker protein will have been deposited on the walls of the well and, upon addition of the antibody/peroxidase conjugate, this conjugate will become attached to the cancer marker protein, thus depositing the conjugate on the walls of the well. If, however, no cancer marker protein was present in the test serum, the antibody/peroxidase conjugate will not adhere to the walls of the wells. Following the incubation with the antibody/peroxidase conjugate, the wells are washed five times, thus removing any conjugate which is not adhered to the walls of the wells. Finally, a substrate for the enzyme comprising hydrogen peroxide in a buffer and ABTS is added to the wells and allowed to develop for ten minutes at room temperature, after which time 20 microliters of a 2 mM sodium azide stop solution are added to each well. The results are read on a microelisa reader. Obviously, if cancer marker protein was present in the test serum and the antibody/peroxidase conjugate was deposited on the walls of the well, color will be developed as the peroxidase in the deposited conjugate acts on the substrate, whereas if no cancer marker protein was present in the test serum there will be no conjugate present on the walls of the well and no color will be developed.

The following examples are now given, though by way of illustration only, to show details of particularly preferred reagents and techniques used in the instant processes.

EXAMPLE 1

This example illustrates the instant process for purification of the cancer marker protein.

Plasma obtained from ten human patients having cancers at eight different sites was pooled, then fractionated with ammonium sulfate. The protein precipitating between 30 and 50% saturation of the aqueous ammonium sulfate solution, which fraction was found to contain all the RNA-releasing activity, was dissolved in approximately 5 ml of the aforementioned TMK buffer, then dialyzed overnight against the same buffer. An aliquot of the dialyzed solution containing approximately 150 mg. of total protein was applied to a 1.5 × 90 cm. column of the molecular sieve resin, Sepharose CL-6B. The column was eluted with the aforementioned TMK buffer and 3 ml fractions were collected. A 200 microliter aliquot of each even-numbered fraction was assayed for RNA-releasing activity as described above.

For control purposes, an exactly similar procedure was followed with pooled plasma from 10 persons who were not suffering from cancer.

Figure 1:
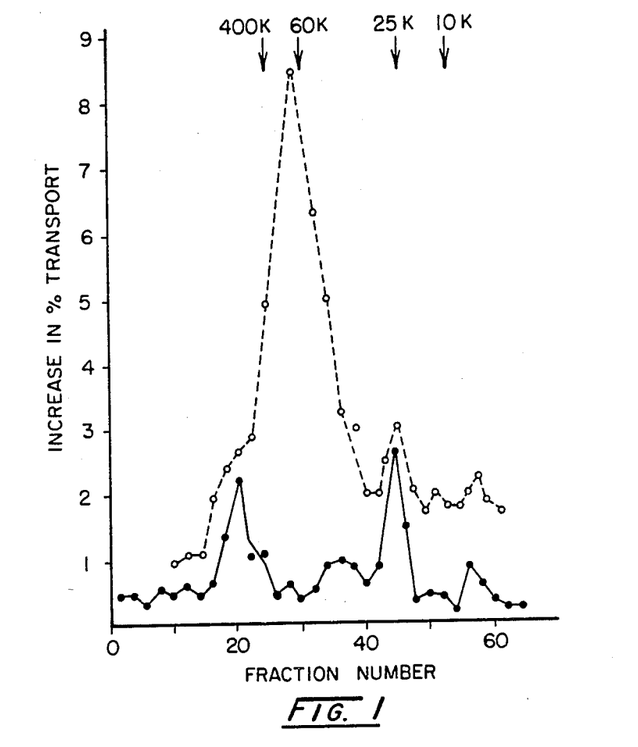
FIG. 1 is a graph showing the distribution of RNA-releasing activity from human cancer patients and healthy individuals obtained by the procedure described in Example 1 below.

The results of the assay are shown in FIG. 1, in which the broken line shows the results obtained from the cancer patients and the continuous line shows the results obtained from the healthy individuals. It will be seen from FIG. 1 that the two profiles are completely different, the cancer patients showing a very strong peak at around 60,000 molecular weight, which is completely absent from the profile of the normal patients. At about fraction number 30, the protein from the cancer patients was showing an increased activity in the assay of approximately 8.5%, equal to an activity of 10 units per milligram of protein in the aliquot.

Further purification of the fractions eluting from the molecular sieve column at a molecular weight of 55,000-70,000 was effected by a further chromatography on a 1.0×10.0 cm column of CM Affi-Gel Blue, in order to remove albumin from the purified cancer marker protein. A sample containing 25.0 mg of protein was suspended in the aforementioned TMK buffer, loaded onto the column and eluted with 0.4M potassium chloride-TMK buffer. Dialysis of eluate and electrophoresis on sodium dodecylsulfate-polyacrylamide gel confirmed that this treatment substantially completely removed albumin from the purified cancer marker preparation. The electrophoretograms produced only a single band corresponding to the cancer marker protein, suggesting that this protein is composed of a single polypeptide chain.

Figure 2:
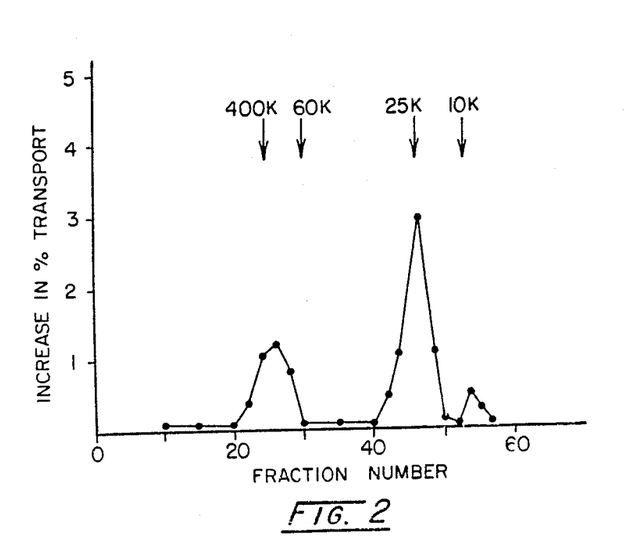
FIG. 2 is a graph, similar to FIG. 1, but showing the RNA-releasing activity distribution from pregnant women.

Since it is known that certain cancer-associated proteins are oncofetal proteins, and since earlier research had indicated that the plasma from pregnant women showed an abnormally high activity in the RNA-releasing activity test, plasma from a pregnant woman was subjected to the purification process already described. The profile obtained is shown in FIG. 2. From this figure, it will be seen that the 60,000 molecular weight peak associated with the cancer marker protein is completely absent from the plasma of the pregnant woman and the RNA releasing activity of the serum is associated with a peak at a molecular weight of 25,000. Accordingly, it appears that the cancer marker protein is completely absent from the plasma of pregnant women and thus pregnancy should not interfere with the instant radioimmunoassay test.

EXAMPLE 2

This example illustrates the instant process for the preparation of an antibody.

The purified cancer marker protein prepared as described in Example 1 was dissolved in normal saline at a concentration of 1.5 milligram of protein per milliliter. 1 ml. of this normal saline solution was then emulsified with 1 ml. of complete Freund's adjuvant using an omni-mixer with a microcontainer immersed in an ice-water bath. The 2 ml. of emulsion thus produced was injected into multiple intradermal sites on the shaved backs of young adult New Zealand white rabbits. This primary immunization was followed by the second immunization approximately 30 days later, the second immunization being performed by the same method as the first except that incomplete Freund's adjuvant was substituted for complete Freund's adjuvant. The animals were bled 1, 2 and 3 weeks after the second immunization and immunodiffusion analyses were conducted to determine the potency and specificity of the antisera obtained. The antisera prepared were absorbed with normal plasma fraction to produce an antibody specific to the cancer marker protein.

It will be apparent to those skilled in the art that numerous changes and modification can be made in the preferred embodiments of the invention described above without departing from the scope of the invention. Accordingly, the whole of the foregoing description is to be construed in an illustrative and not in a limitative sense, the scope of the invention being defined solely by the appended claims.

We claim:
1. A protein preparation comprising a cancer-associated phosphoprotein having the following characteristics:
   (a) not being precipitated by 30% saturated aqueous ammonium sulfate solution at 25° C.;
   (b) having a molecular weight of approximately 60,000,
   (c) being precipitated from aqueous solution by 3.3% streptomycin sulfate;
   (d) having substantially no autophosphorylation activity but being phosphorylated with adenosine triphosphate in the presence of an exogenous protein kinase;
   (e) having substantially no protein kinase activity;
   (f) having the capacity to liberate ribonucleic acid from cell nuclei;
   (g) being substantially free of albumin; and
   (h) normally absent from the maternal blood of non-cancerous normal pregnant mammals of the species in which said protein is being determined,
   said protein preparation having an RNA-releasing activity of at least about 10 units per milligram of total protein in said protein preparation.

2. A protein preparation according to claim 1 having an RNA-releasing activity of about 20 units per milligram of total protein in said protein preparation.

3. A process for producing an antibody serum containing antibodies to a cancer-associated phosphoprotein, said process comprising:
   introducing into the bloodstream of a second mammal a protein preparation derived from a first mammal, said preparation having the following characteristics:
   (a) not being precipitated by 30% saturated aqueous ammonium sulfate solution at 25° C.;
   (b) having a molecular weight of approximately 60,000,
   (c) being precipitated from aqueous solution by 3.3% streptomycin sulfate;
   (d) having substantially no autophosphorylation activity but being phosphorylated with adenosine triphosphate in the presence of an exogenous protein kinase;
   (e) having substantially no protein kinase activity;
   (f) having the capacity to liberate ribonucleic acid from cell nuclei;
   (g) being substantially free of albumin; and
   (h) normally absent from the maternal blood of non-cancerous normal pregnant mammals of the species in which said protein is being determined,
   said protein preparation having an RNA-releasing activity of at least about 10 units per milligram of total protein in said protein preparation, allowing said protein preparation to remain in said bloodstream of said second mammal for at least about 7 days;
   removing blood from said second mammal;
   preparing serum from said blood; and
   absorbing said serum with plasma from a normal mammal of the same species as said first mammal to produce said antibody serum.

4. A process according to claim 3 wherein said protein preparation is introduced into said bloodstream of said mammal together with an immunostimulating adjuvant.

5. A process according to claim 4 wherein said imunostimulating adjuvant is complete or incomplete Freund's adjuvant.

6. A process according to claim 3 wherein said protein preparation is administered into said mammal by intradermal injection.

7. A process according to claim 3 wherein said mammal is given a primary immunization with said protein preparation and an immunostimulating adjuvant and a second immunization with said protein preparation and an immunostimulating adjuvant at least about 7 days after said primary immunization, and wherein said blood is removed from said mammal at least about 3 days after said second immunization.

8. A process according to claim 3 wherein said protein preparation is derived from plasma of a human suffering from cancer.

9. A process according to claim 8 wherein said protein preparation has an RNA-releasing activity of about 20 units per milligram of total protein in said protein preparation.

10. A process according to claim 3 wherein said mammal is a rabbit.

11. A process according to claim 3 wherein said protein preparation is prepared by:
(a) separating from the plasma of a mammal suffering from cancer the fraction of plasma protein which is not precipitated by 30% saturated aqueous ammonium sulfate solution;
(b) dispersing said fraction of plasma protein in a buffer and dialyzing the resultant protein solution against said buffer;
(c) separating the fraction of said dialyzed protein having a molecular weight of about 60,000; and
(d) removing substantially all albumin from said 60,000 molecular weight fraction.

12. A process according to claim 11 wherein said protein preparation is derived from plasma of a human suffering from cancer.

13. A process according to claim 12 wherein said protein preparation has an RNA-releasing activity of about 20 units per milligram of total protein in said protein preparation.

14. An antibody preparation substantially free of antibodies to normal plasma fraction, said antibody preparation being precipitated by 35% saturated aqueous ammonium sulfate solution and being capable of forming a conjugate with a cancer-associated phosphoprotein having the following characteristics:
(a) not being precipitated by 30% saturated aqueous ammonium sulfate solution at 25° C.;
(b) having a molecular weight of approximately 60,000,
(c) being precipitated from aqueous solution by 3.3% streptomycin sulfate;
(d) having substantially no autophosphorylation activity but being phosphorylated with adenosine triphosphate in the presence of an exogenous protein kinase;
(e) having substantially no protein kinase activity;
(f) having the capacity to liberate ribonucleic acid from cell nuclei;
(g) being substantially free of albumin; and
(h) normally absent from the maternal blood of noncancerous normal pregnant mammals of the species in which said protein is being determined, said antibody preparation forming a visible precipitate with said cancer-associated phosphoprotein when they are diffused toward one another in ager gel, but said antibody preparation not being capable of forming a conjugate with the 25K protein fraction from human plasma nor the 35K protein fraction from rat plasma.

15. A method for determining the presence in a mammal of a cancer-associated phosphoprotein having the following characteristics:
(a) not being precipitated by 30% saturated aqueous ammonium sulfate solution at 25° C.;
(b) having a molecular weight of approximately 60,000;
(c) being precipitated from aqueous solution by 3.3% streptomycin sulfate;
(d) having substantially no autophosphorylation activity but being phosphorylated with adenosine triphosphate in the presence of an exogenous protein kinase;
(e) having substantially no protein kinase activity;
(f) having the capacity to liberate ribonucleic acid from cell nuclei; and
(g) not being present in the maternal blood of noncancerous normal pregnant mammals of the species in which said protein is being determined; comprising the steps of producing antibodies to said antigen;
contacting said antibodies with biological material of said mammal; and
determining the presence of a reaction product formed between said antibodies and said antigen.

16. A method according to claim 15 wherein the presence of said reaction product is determined by radioimmunoassay.

17. A method according to claim 15 wherein the presence of said reaction product is determined by ELISA assay.

18. A method according to claim 15 wherein said biological material is the plasma of said mammal.

19. A method according to claim 15 wherein said antibodies are derived from a second mammal immunized with said antigen.

20. A method to determine the quantity of a cancer-associated phosphoprotein present in the blood protein of a mammal comprising
(a) providing blood protein from a mammal;
(b) mixing said blood protein with an antibody serum containing antibodies to said cancer-associated phosphoprotein, said antibody serum formed by:
1. introducing into the bloodstream of a second mammal a protein preparation derived from a first mammal, said protein preparation having the following characteristics:
(i) not being precipitated by 30% saturated aqueous ammonium sulfate solution at 25° C.;
(ii) a molecular weight of approximately 60,000;
(iii) being precipitated from aqueous solution by 3.3% streptomycin sulfate;
(iv) substantially no autophosphorylation activity, but being phosphorylated with adenosine triphosphate in the presence of an exogenous protein kinase;
(v) substantially no protein kinase activity;
(vi) the capacity to liberate ribonucleic acid from cell nuclei;
(vii) substantially free of albumin;

(viii) an RNA-releasing activity of at least about 10 units per milligram of total protein in said protein preparation; and (ix) normally absent from the maternal blood of non-cancerous normal pregnant mammals of the species in which said protein is being determined;

2. allowing said protein preparation to remain in said bloodstream of said second mammal for at least 7 days;
3. removing blood from said second mammal;
4. preparing serum from said blood; and
5. absorbing said serum with plasma from a normal mammal of the same species as said first mammal to produce said antibody serum; and (c) determining the quantity of said cancer associated phosphoprotein reactive with said antibody serum by radioimmunoassay.

21. A method to determine the presence of a cancer-associated phosphoprotein in a mammal comprising providing a serum sample from said mammal and undertaking an ELISA assay using said serum sample and an antibody serum containing antibodies to said cancer-associated phosphoprotein, said antibody serum formed by:

1. introducing into the bloodstream of a second mammal a protein preparation derived from a first mammal, said protein preparation having the following characteristics:
    (a) not being precipitated by 30% saturated aqueous ammonium sulfate solution at 25° C.;
    (b) a molecular weight of approximately 60,000;
    (c) being precipitated from aqueous solution by 3.3% streptomycin sulfate;
    (d) substantially no autophosphorylation activity but being phosphorylated with adenosine triphosphate in the presence of an exogenous protein kinase;
    (e) substantially no protein kinase activity;
    (f) the capacity to liberate ribonucleic acid from cell nuclei;
    (g) substantially free of albumin; and
    (h) an RNA-releasing activity of at least about 10 units per milligram of total protein in said protein preparation;
    (i) normally absent from the maternal blood of non-cancerous normal pregnant mammals of the species in which said protein is being determined;

2. allowing said protein preparation to remain in said bloodstream of said second mammal for at least about 7 days;
3. removing blood from said second mammal;
4. preparing serum from said blood; and
5. absorbing said serum with plasma from a normal mammal of the same species as said first mammal to produce said antibody serum.

22. A protein preparation comprising a cancer-associated phosphoprotein having the following characteristics:
    (a) not being precipitated by 30% saturated aqueous ammonium sulfate solution at 25° C.;
    (b) having a molecular weight of approximately 60,000,
    (c) being precipitated from aqueous solution by 3.3% streptomycin sulfate;
    (d) having substantially no autophosphorylation activity but being phosphorylated with adenosine triphosphate in the presence of an exogenous protein kinase;
    (e) having substantially no protein kinase activity;
    (f) having the capacity to liberate ribonucleic acid from cell nuclei;
    (g) being substantially free of plasma proteins including albumin, and
    (h) normally absent from the maternal blood of non-cancerous normal pregnant mammals of the species in which said protein is being determined, said protein preparation having an RNA-releasing activity of at least about 10 units per milligram of total protein in said protein preparation.

* * * * *